US012036051B2

(12) United States Patent
Morita

(10) Patent No.: US 12,036,051 B2
(45) Date of Patent: *Jul. 16, 2024

(54) TOMOSYNTHESIS IMAGING SUPPORT APPARATUS, METHOD, AND PROGRAM

(71) Applicant: FUJIFILM CORPORATION, Tokyo (JP)

(72) Inventor: Junya Morita, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/317,976

(22) Filed: May 16, 2023

(65) Prior Publication Data

US 2023/0277141 A1    Sep. 7, 2023

Related U.S. Application Data

(62) Division of application No. 16/695,065, filed on Nov. 25, 2019, now Pat. No. 11,751,822.

(30) Foreign Application Priority Data

Dec. 7, 2018    (JP) .................................. 2018-230272

(51) Int. Cl.
*A61B 6/02*  (2006.01)
*A61B 6/00*  (2024.01)
(Continued)

(52) U.S. Cl.
CPC ............ *A61B 6/025* (2013.01); *A61B 6/0487* (2020.08); *A61B 6/4476* (2013.01); *A61B 6/502* (2013.01);
(Continued)

(58) Field of Classification Search
CPC ......... A61B 6/502; A61B 8/0825; A61B 6/54; A61B 6/5211; A61B 6/5217; A61B 6/545;
(Continued)

(56) References Cited

U.S. PATENT DOCUMENTS

2009/0143674 A1    6/2009   Nields et al.
2010/0054557 A1    3/2010   Morita et al.
(Continued)

FOREIGN PATENT DOCUMENTS

EP    2070478 A1    6/2009
EP    2757528 A1    7/2014
(Continued)

OTHER PUBLICATIONS

Extended European Search Report dated May 11, 2020, issued in corresponding EP Patent Application No. 19211828.9.
(Continued)

*Primary Examiner* — John Villecco
*Assistant Examiner* — Courtney Joan Nelson
(74) *Attorney, Agent, or Firm* — SOLARIS Intellectual Property Group, PLLC

(57) ABSTRACT

An information acquisition unit acquires at least one information item of subject information, imaging condition information, or positioning information. Next, a body movement feature derivation unit derives body movement feature information indicating a feature of body movement of a breast which occurs at the time of the tomosynthesis imaging. A storage stores correspondence information in which the derived body movement feature information corresponds to at least one information item of the subject information, the imaging condition information, or the positioning information.

11 Claims, 13 Drawing Sheets

(51) Int. Cl.
*A61B 6/04* (2006.01)
*A61B 6/50* (2024.01)
*G06T 7/00* (2017.01)

(52) U.S. Cl.
CPC .. *G06T 7/0014* (2013.01); *G06T 2207/20084* (2013.01); *G06T 2207/30068* (2013.01)

(58) Field of Classification Search
CPC ..... A61B 6/488; A61B 10/0041; A61B 90/17; A61B 6/527; A61B 8/13; A61B 6/5264; A61B 6/025; A61B 6/0487; A61B 6/4476; G06T 2207/30068; G06T 7/0012; G06T 2207/20084; G06T 2207/30004; G06T 7/33; G06T 7/0014; G16H 50/20; G16H 30/40; G16H 30/20
See application file for complete search history.

(56) References Cited

U.S. PATENT DOCUMENTS

| | | |
|---|---|---|
| 2012/0033868 A1 | 2/2012 | Ren et al. |
| 2012/0059239 A1* | 3/2012 | Yamaguchi .......... A61B 6/5241 600/407 |
| 2013/0279825 A1 | 10/2013 | Liao et al. |
| 2019/0059841 A1 | 2/2019 | Palma et al. |

FOREIGN PATENT DOCUMENTS

| | | |
|---|---|---|
| JP | 2009-247521 A | 10/2009 |
| JP | 2010-051455 A | 3/2010 |
| JP | 2010-51456 A | 3/2010 |
| JP | 2010-253245 A | 11/2010 |
| JP | 2016-064119 A | 4/2016 |
| WO | 2015/107866 A1 | 7/2015 |

OTHER PUBLICATIONS

English language translation of the following: Office action dated Feb. 8, 2022 from the JPO in a Japanese patent application No. 2018-230272 corresponding to the instant patent application.
Machine translation of JP2009247521A (Year 2009).
Arnau Oliver et al., "A novel breast tissue density classification methodology .", IEEE Transactions on Information Technology in Biomedicine 12.1 (2008) : 55-65 (Year 2008).
Non-Final Office Action issued by USPTO on Mar. 10, 2022, in related U.S. Appl. No. 16/695,065.
Final Office Action issued by USPTO on Jul. 1, 2022, in related U.S. Appl. No. 16/695,065.
Advisory Action issued by USPTO on Oct. 12, 2022, in related U.S. Appl. No. 16/695,065.
Non-Final Office Action issued by USPTO on Nov. 1, 2022, in related U.S. Appl. No. 16/695,065.
Final Office Action issued by USPTO on Feb. 21, 2023, in related U.S. Appl. No. 16/695,065.

* cited by examiner

FIG. 17

51
CLASSIFICATION OF MOVEMENT: "GRADUAL MOVEMENT IN CERTAIN DIRECTION", COMPRESSION PRESSURE: EQUAL TO OR SMALLER THAN THRESHOLD
→ IN PREVIOUS IMAGING, BODY MOVEMENT BEING GRADUALLY MOVED IN CERTAIN DIRECTION OCCURS UNDER COMPRESSION PRESSURE X [N]. PLEASE TAKE IMAGE WITH INCREASED COMPRESSION PRESSURE.

52
CLASSIFICATION OF MOVEMENT: "RAPID CHANGE"
→ IN PREVIOUS IMAGING, BODY MOVEMENT RAPIDLY CHANGING OCCURS. PLEASE ASK PATIENT NOT TO SUDDENLY MOVE DURING IMAGING AND TAKE IMAGE.

53
CLASSIFICATION OF MOVEMENT: OTHER THAN "NO BODY MOVEMENT", TYPE OF BREAST: "FATTY BREAST" or THICKNESS OF BREAST: EQUAL TO OR GREATER THAN THRESHOLD
→ IT IS BREAST THAT BODY MOVEMENT IS LIKELY TO OCCUR. PLEASE TAKE IMAGE WITH ATTENTION TO COMPRESSION PRESSURE AND POSITIONING.

54
CLASSIFICATION OF MOVEMENT: "GRADUAL MOVEMENT IN CERTAIN DIRECTION"
IMAGING DIRECTION: MLO
POSITIONING INFORMATION: PECTORALIS MAJOR MUSCLE AREA IS EQUAL TO OR GREATER THAN THRESHOLD
→ IN PREVIOUS IMAGING, BODY MOVEMENT BEING GRADUALLY MOVED IN CERTAIN DIRECTION OCCURS AT POSITIONING IN WHICH PECTORALIS MAJOR MUSCLE IS GREATLY REFLECTED. PLEASE PAY ATTENTION TO POSITIONING AND TAKE IMAGE.

FIG. 18

60
PATIENT ID: XXXX
PATIENT NAME: FUJI HANAKO

IN PREVIOUS IMAGING, BODY MOVEMENT RAPIDLY CHANGING OCCURS. PLEASE ASK PATIENT NOT TO SUDDENLY MOVE DURING IMAGING AND TAKE IMAGE.

TOMOSYNTHESIS IMAGING SUPPORT APPARATUS, METHOD, AND PROGRAM

CROSS REFERENCE TO RELATED APPLICATIONS

The present application is a divisional application of U.S. application Ser. No. 16/695,065, filed on Nov. 25, 2019, which claims priority under 35 U.S.C. § 119 to Japanese Patent Application No. 2018-230272, filed on Dec. 7, 2018. Each of the above applications is hereby expressly incorporated by reference, in its entirety, into the present application.

BACKGROUND

Technical Field

The present disclosure relates to a tomosynthesis imaging support apparatus, a tomosynthesis imaging support method, and a tomosynthesis imaging support program that support tomographic imaging.

Related Art

In recent years, in radiation image capturing apparatuses using radiation such as X-rays and gamma rays, in order to observe an affected part in more detail, tomosynthesis imaging has been proposed in which imaging is performed by moving a radiation source to emit radiation to a subject from a plurality of radiation source positions and a plurality of projection images acquired by the imaging are added up to generate a tomographic image in which a desired tomographic plane is emphasized. In the tomosynthesis imaging, a plurality of projection images are acquired by imaging the subject at a plurality of radiation source positions by moving the radiation source in parallel to a radiation detector or moving the radiation source so as to draw a circular or elliptical arc according to the characteristics of the imaging apparatus and required tomographic images, and the projection images are reconstructed using, for example, a back projection method, such as a simple back projection method or a filtered back projection method, to generate a tomographic image.

By generating such a tomographic image on a plurality of tomographic planes of the subject, it is possible to separate structures overlapping each other in a depth direction in which the tomographic planes are aligned. Therefore, it is possible to find a lesion that has been difficult to detect in a two-dimensional image acquired by simple imaging in the related art. The simple imaging is an imaging method for acquiring one two-dimensional image, which is a transmission image of a subject, by emitting radiation to the subject once.

On the other hand, the tomosynthesis imaging has a problem that a reconstructed tomographic image is blurred due to the mechanical error of the imaging apparatus and the influence of body movement of the subject due to the time difference of imaging at the plurality of radiation source positions. In a case where the tomographic image is blurred as described above, it is difficult to find a lesion such as minute calcification, which is useful for early detection of breast cancer, particularly in a case where the breast is a subject.

For this reason, a method of correcting body movement in the case of generating a tomographic image from a projection image acquired by tomosynthesis imaging has been proposed.

For example, JP2016-064119A has proposed a method in which a plurality of tomographic plane projection images are acquired by projecting the pixel values of a plurality of projection images acquired by tomosynthesis imaging onto coordinate positions on a desired tomographic plane of a subject based on the positional relationship between the radiation source position and a radiation detector at the time of imaging for each of the plurality of projection images while maintaining the pixel values of the plurality of projection images, positional shift between the plurality of tomographic plane projection images is corrected, and a tomographic image is generated from the plurality of tomographic plane projection images subjected to positional shift correction.

In a case where tomosynthesis imaging is performed, it is first necessary to contrive a means for preventing body movement at the time of the imaging. However, there are various reasons that body movement occurs. For example, the way in which body movement occurs differs depending on a feature of a subject, an imaging condition, and a positioning manner of the subject, and the like. For this reason, it is difficult for an operator to appropriately estimate what kind of body movement occurs in each tomosynthesis imaging and to appropriately contrive a means for preventing body movement.

SUMMARY OF THE INVENTION

The present invention has been made in view of the aforementioned circumstances, and the object of the present invention is to make it possible to appropriately estimate what kind of body movement occurs at the time of tomosynthesis imaging.

A tomosynthesis imaging support apparatus according to the present disclosure comprises an information acquisition unit that acquires at least one information item of subject information indicating a feature of a subject, imaging condition information indicating imaging conditions at the time of tomosynthesis imaging, or positioning information indicating positioning of the subject in a case where a plurality of projection images corresponding to each of a plurality of radiation source positions are acquired by performing the tomosynthesis imaging in which a radiation source is moved relative to a detection unit in order to emit radiation to the subject at the plurality of radiation source positions according to movement of the radiation source, a body movement feature derivation unit that derives body movement feature information indicating a feature of body movement of the subject that occurs at the time of the tomosynthesis imaging, and a storage that stores correspondence information in which at least one information item of the subject information, the imaging condition information, or the positioning information corresponds to the body movement feature information.

"The radiation source is moved relative to the detection unit" includes a case of moving only the radiation source, a case of moving only the detection unit, and a case of moving both the radiation source and the detection unit.

Example of the subject information includes a size and a thickness of the subject, a mammary gland quantity in a case where the subject is a breast, and a patient name. The imaging condition includes an imaging time, a compression force in a case where the subject is the breast, an imaging direction (cranio-caudal (CC) direction and medio-lateral oblique (MLO) direction), and a technician name, and the like.

In the tomosynthesis imaging support apparatus according to the present disclosure, the correspondence information may be a database in which at least one information item of the subject information, the imaging condition information, or the positioning information corresponds to the body movement feature information.

In addition, in the tomosynthesis imaging support apparatus according to the present disclosure, the correspondence information may be a learned model in which learning is performed such that the body movement feature information is output by inputting at least one information item of the subject information, the imaging condition information, or the positioning information.

Additionally, in the tomosynthesis imaging support apparatus according to the present disclosure, the body movement feature information may include at least one of a positional shift amount based on body movement between the plurality of projection images, a representative value of the positional shift amount for each region in a case where the subject is divided into a plurality of the regions, or classification of body movement according to the positional shift amount.

Furthermore, in the tomosynthesis imaging support apparatus according to the present disclosure, the subject may be a breast.

In this case, the subject information may include at least one of a size of the breast included in the projection image, a thickness of the breast, a type of the breast, or information specifying a patient.

In the tomosynthesis imaging support apparatus according to the present disclosure, the imaging condition information may include at least one of an imaging time at the time of the tomosynthesis imaging, a compression force of the breast, an imaging direction of the breast, or information specifying a technician who performs imaging.

In addition, the tomosynthesis imaging support apparatus according to the present disclosure may further comprise a body movement feature acquisition unit that acquires at least one information item of new subject information, new imaging condition information, or new positioning information, and acquires the body movement feature information indicating the feature of body movement of the subject that occurs at the time of new tomosynthesis imaging according to the acquired information, with reference to the correspondence information.

In addition, the tomosynthesis imaging support apparatus according to the present disclosure may further comprise an advice derivation unit that derives an imaging advice at the time of the tomosynthesis imaging according to the acquired body movement feature information.

In addition, in the tomosynthesis imaging support apparatus according to the present disclosure, the advice derivation unit may derive the imaging advice according to at least one information item of the subject information, the imaging condition information, or the positioning information.

In addition, the tomosynthesis imaging support apparatus according to the present disclosure may further comprise a display controller that displays the acquired body movement feature information.

Additionally, the tomosynthesis imaging support apparatus according to the present disclosure may further comprise a display controller that displays at least one of the body movement feature information or the imaging advice.

A tomosynthesis imaging support method according to the present disclosure acquires at least one information item of subject information indicating a feature of the subject, imaging condition information indicating imaging conditions at the time of tomosynthesis imaging, or positioning information indicating positioning of the subject in a case where a plurality of projection images corresponding to each of a plurality of radiation source positions are acquired by performing the tomosynthesis imaging in which a radiation source is moved relative to a detection unit in order to emit radiation to the subject at the plurality of radiation source positions according to movement of the radiation source, derives body movement feature information indicating a feature of body movement of the subject that occurs at the time of the tomosynthesis imaging, and stores correspondence information in which at least one information item of the subject information, the imaging condition information, or the positioning information corresponds to the body movement feature information.

A tomosynthesis imaging support program according to the present disclosure causes a computer to execute a step of acquiring at least one information item of subject information indicating a feature of a subject, imaging condition information indicating imaging conditions at the time of tomosynthesis imaging, or positioning information indicating positioning of the subject in a case where a plurality of projection images corresponding to each of a plurality of radiation source positions are acquired by performing the tomosynthesis imaging in which a radiation source is moved relative to a detection unit in order to emit radiation to the subject at the plurality of radiation source positions according to movement of the radiation source, a step of deriving body movement feature information indicating a feature of body movement of the subject that occurs at the time of the tomosynthesis imaging, and a step of storing correspondence information in which at least one information item of the subject information, the imaging condition information, or the positioning information corresponds to the body movement feature information.

Another tomosynthesis imaging support apparatus according to the present disclosure comprises a memory that stores a command to be executed by a computer, and a processor configured to execute the stored commands. The processor executes processing that acquires at least one information item of subject information indicating a feature of a subject, imaging condition information indicating imaging conditions at the time of tomosynthesis imaging, or positioning information indicating positioning of the subject in a case where a plurality of projection images corresponding to each of a plurality of radiation source positions are acquired by performing the tomosynthesis imaging in which a radiation source is moved relative to a detection unit in order to emit radiation to the subject at the plurality of radiation source positions according to movement of the radiation source, derives body movement feature information indicating a feature of body movement of the subject that occurs at the time of the tomosynthesis imaging, and stores the correspondence information in which at least one information item of the subject information, the imaging condition information, or the positioning information corresponds to the body movement feature information.

According to the present disclosure, it is possible to appropriately estimate what kind of body movement occurs at the time of the tomosynthesis imaging.

BRIEF DESCRIPTION OF THE DRAWINGS

FIG. 17 is a diagram showing teacher data.

FIG. 18 is a diagram showing a display screen for an imaging advice.

DETAILED DESCRIPTION

Figure 1:
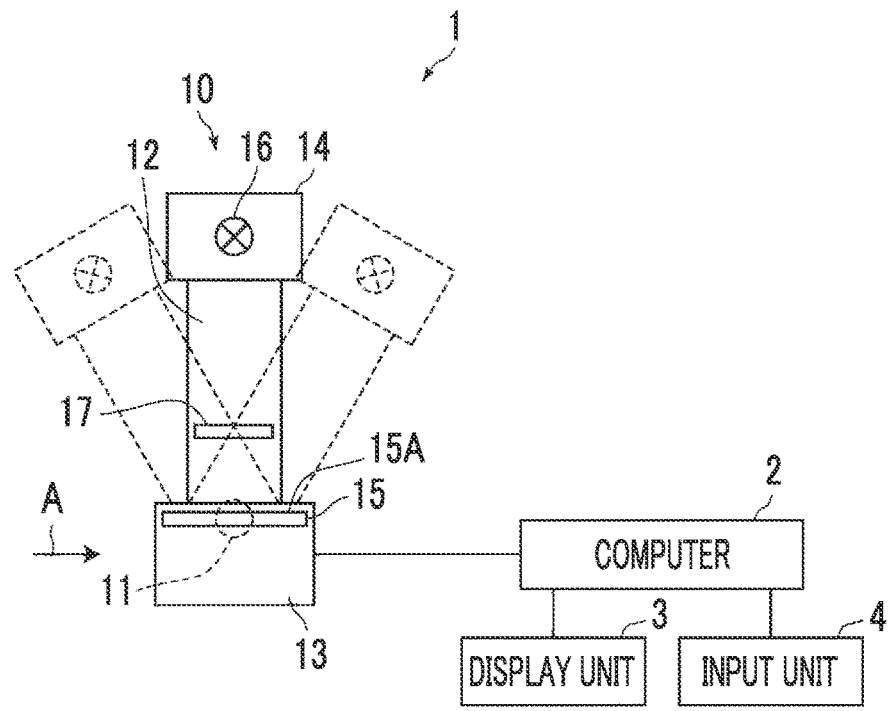
FIG. 1 is a schematic configuration diagram of a radiation image capturing apparatus to which a tomosynthesis imaging support apparatus according to the embodiment of the present disclosure is applied.
Figure 2:
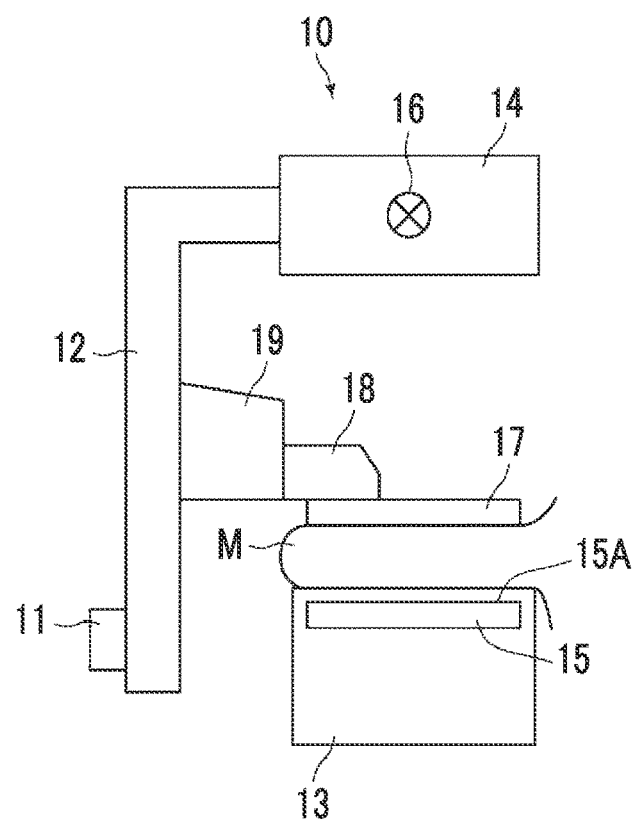
FIG. 2 is a diagram of the radiation image capturing apparatus as viewed from the direction of arrow A in FIG. 1.

Hereinafter, the embodiments of the present disclosure will be described with reference to the diagrams. FIG. 1 is a schematic configuration diagram of a radiation image capturing apparatus to which a tomosynthesis imaging support apparatus according to the embodiment of the present disclosure is applied, and FIG. 2 is a diagram of the radiation image capturing apparatus as viewed from the direction of arrow A in FIG. 1. A radiation image capturing apparatus 1 is a mammography imaging apparatus that acquires a plurality of radiation images, that is, a plurality of projection images, by imaging a breast M, which is a subject, from a plurality of radiation source positions in order to generate a tomographic image by performing tomosynthesis imaging of the breast. As shown in FIG. 1, the radiation image capturing apparatus 1 comprises an imaging unit 10, a computer 2 connected to the imaging unit 10, and a display unit 3 and an input unit 4 which are connected to the computer 2.

The imaging unit 10 comprises an arm unit 12 connected to a base (not shown) by a rotary shaft 11. An imaging table 13 is attached to one end portion of the arm unit 12, and a radiation emission unit 14 is attached to the other end portion so as to face the imaging table 13. The arm unit 12 is configured so that only the end portion to which the radiation emission unit 14 is attached can rotate. Therefore, it is possible to rotate only the radiation emission unit 14 with the imaging table 13 fixed. The rotation of the arm unit 12 is controlled by the computer 2.

The imaging table 13 comprises a radiation detector 15 such as a flat panel detector therein. The radiation detector 15 has a detection surface 15A of radiation such as X-rays. In addition, a circuit board on which a charge amplifier for converting a charge signal read from the radiation detector 15 into a voltage signal, a correlated double sampling circuit for sampling the voltage signal output from the charge amplifier, an analog digital (AD) conversion unit for converting the voltage signal into a digital signal, and the like are provided is provided inside the imaging table 13. The radiation detector 15 corresponds to a detection unit. Although the radiation detector 15 is used as the detection unit in the present embodiment, the detection unit is not limited to the radiation detector 15 as long as radiation can be detected and converted into an image.

The radiation detector 15 can perform recording and reading of a radiation image repeatedly. A so-called direct-type radiation detector that directly converts radiation, such as X-rays, into electric charges may be used, or a so-called indirect-type radiation detector that converts radiation into visible light and then converts the visible light into a charge signal may be used. As a method of reading a radiation image signal, it is desirable to use a so-called thin film transistor (TFT) reading method in which a radiation image signal is read by ON and OFF of a TFT switch, or a so-called optical reading method in which a radiation image signal is read by emission of reading light. However, other methods may also be used without being limited to the above methods.

A radiation source 16 that emits radiation such as X-rays is housed inside the radiation emission unit 14. The timing of emission of radiation from the radiation source 16, and a radiation generation condition in the radiation source 16, that is, selection of target and filter materials, a tube voltage, an emission time, and the like are controlled by the computer 2.

The arm unit 12 includes compression plate 17 disposed above the imaging table 13 to compress the breast M, a support unit 18 that supports the compression plate 17, and a moving mechanism 19 that moves the support unit 18 in the vertical direction in FIGS. 1 and 2. Information of the distance between the compression plate 17 and the imaging table 13, that is, a compression thickness of the breast M is input to the computer 2.

The display unit 3 is a display device such as a cathode ray tube (CRT) or a liquid crystal monitor, and displays a message required for the operation, and the like in addition to a projection image and a tomographic image acquired as described later. The display unit 3 may include a speaker for outputting sound.

The input unit 4 includes an input device such as a keyboard, a mouse, or a touch panel, and receives an operation of the radiation image capturing apparatus 1 by the operator. In addition, the input unit 4 receives an input of various kinds of information such as imaging conditions, which are required to perform the tomosynthesis imaging. Furthermore, in the present embodiment, the input unit 4 receives the input by the operator of at least one information item of subject information indicating a feature of the breast M that is the subject, imaging condition information indicating the imaging conditions at the time of the tomosynthesis imaging, or positioning information indicating positioning of the breast M. Each unit of the radiation image capturing apparatus 1 operates according to the information input from the input unit 4.

A tomosynthesis imaging support program according to the present embodiment is installed in the computer 2. In the present embodiment, the computer may be a workstation or a personal computer that is directly operated by the operator, or may be a server computer connected to these through a network. The tomosynthesis imaging support program is distributed in a state of being recorded on a recording medium such as a digital versatile disc (DVD) or a compact disc read only memory (CD-ROM), and is installed in the computer from the recording medium. Alternatively, the tomographic imaging support program is stored in a storage device of a server computer connected to the network, or in a network storage (hereinafter, referred to as an external storage device) so as to be accessible from the outside, and is downloaded and installed in the computer as necessary.

Figure 3:
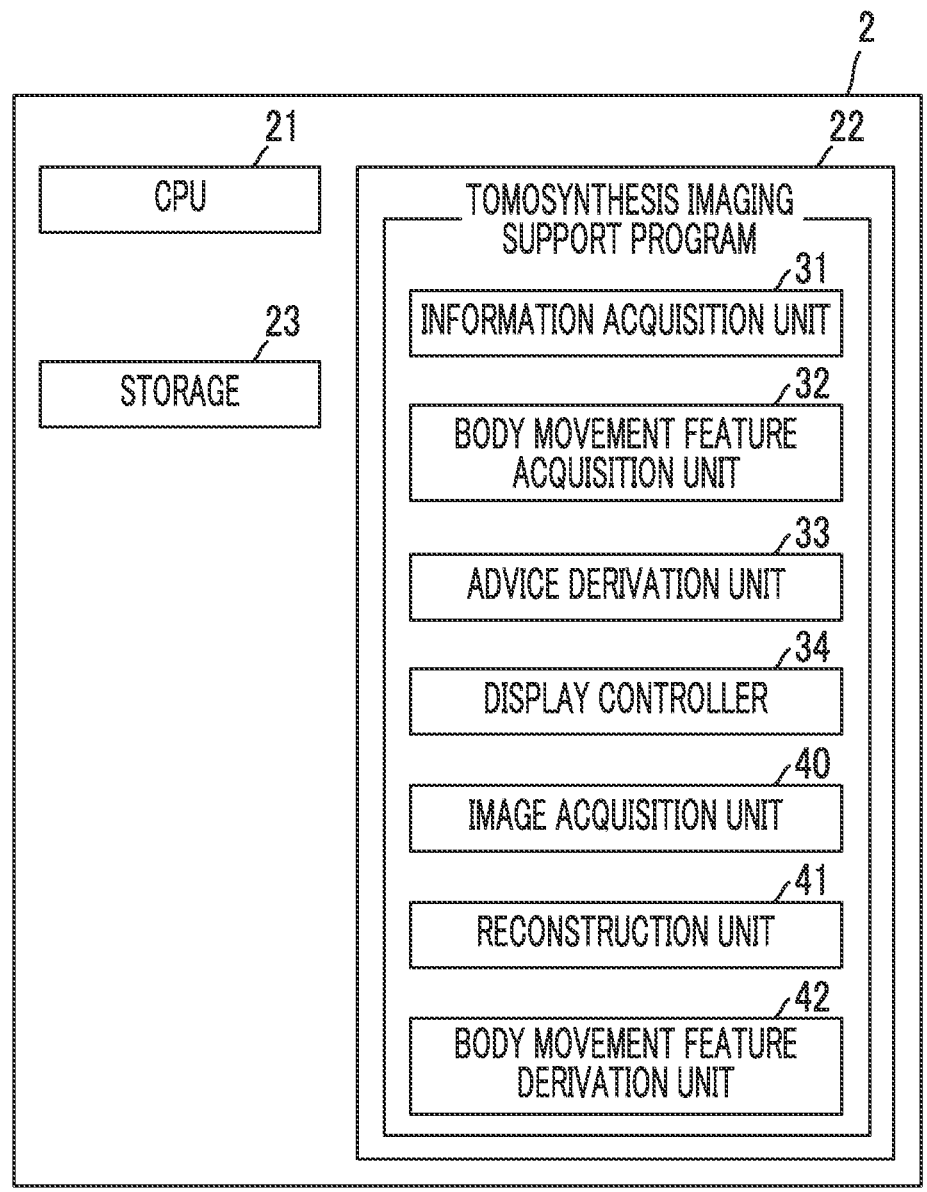
FIG. 3 is a diagram showing the schematic configuration of a tomosynthesis imaging support apparatus realized by installing a tomosynthesis imaging support program in a computer in the present embodiment.

FIG. 3 is a diagram showing the schematic configuration of the tomosynthesis imaging support apparatus realized by installing the tomosynthesis imaging support program according to the present embodiment in the computer 2. As shown in FIG. 3, the tomosynthesis imaging support apparatus comprises a central processing unit (CPU) 21, a memory 22, and a storage 23 as the configuration of a standard computer.

The storage 23 includes a storage device such as a hard disk drive or a solid state drive (SSD), and stores various kinds of information including a program for driving each unit of the radiation image capturing apparatus 1 and the tomosynthesis imaging support program. In addition, the storage 23 also stores the projection image acquired by tomosynthesis imaging, and the tomographic image generated as described later.

The memory 22 temporarily stores programs and the like stored in the storage 23 so that the CPU 21 executes various kinds of processing. As processing to be executed by the CPU 21, the tomosynthesis imaging support program defines information acquisition processing that acquires at least one information item of subject information indicating a feature of the breast M which is the subject, imaging condition information indicating the imaging conditions at the time of the tomosynthesis imaging, or positioning information indicating positioning of the breast M, body movement feature acquisition processing that acquires body movement feature information indicating a feature of body movement of the breast M which occurs at the time of the tomosynthesis imaging according to the acquired information, with reference to a database as described later, advice derivation processing that derives an imaging advice at the time of the tomosynthesis imaging according to the body movement feature information, and display control processing that displays at least one of the body movement feature information or the imaging advice on the display unit 3.

Then, the CPU 21 executes these kinds of processing according to the tomosynthesis imaging support program, so that the computer 2 functions as an information acquisition unit 31, a body movement feature acquisition unit 32, an advice derivation unit 33, and a display controller 34.

In the present embodiment, the computer 2 causes the imaging unit 10 to perform tomosynthesis imaging and functions as an image acquisition unit 40 that acquires the plurality of projection images of the breast M each corresponding to the plurality of radiation source positions, a reconstruction unit 41 that generates the tomographic image on at least one tomographic plane of the breast M by reconstructing the plurality of projection images, and a body movement feature derivation unit 42 that derives the body movement feature information from a positional shift amount between projection images.

First, the image acquisition unit 40 and the reconstruction unit 41 will be described. In the case of performing image acquisition processing, the radiation source 16 is moved by rotating the arm unit 12 around the rotary shaft 11, radiation is emitted to the breast M as a subject at a plurality of radiation source positions according to the movement of the radiation source 16 under the predetermined imaging conditions for tomosynthesis imaging, radiation transmitted through the breast M are detected by the radiation detector 15, and a plurality of projection images Gi (i=1 to n, where n is the number of radiation source positions; for example, n=15) at a plurality of radiation source positions are acquired by the image acquisition unit 40.

Figure 4:
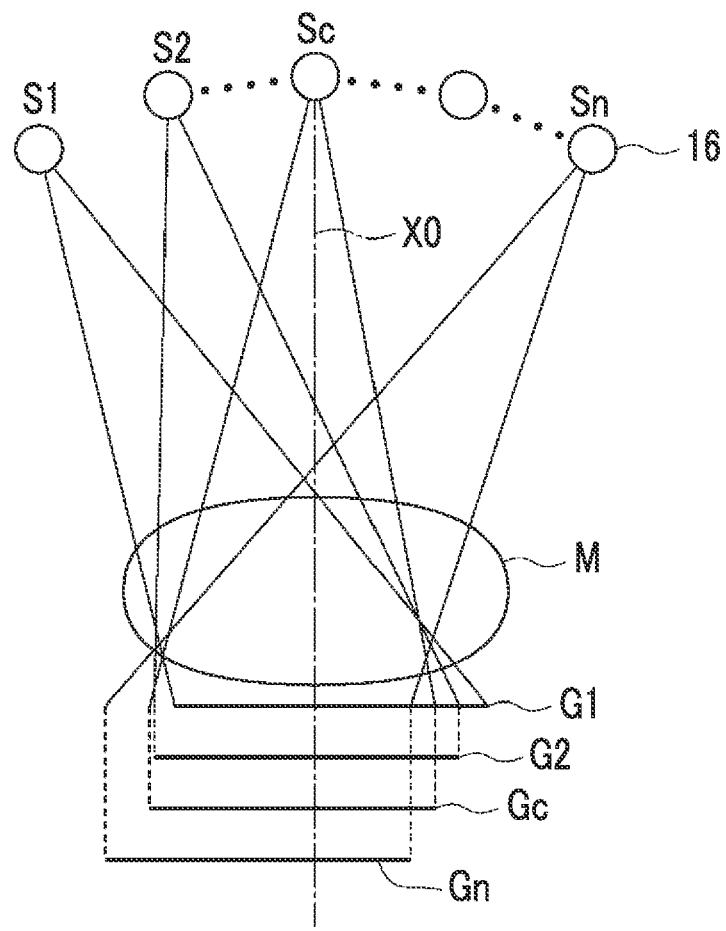
FIG. 4 is a diagram illustrating the acquisition of a projection image.

FIG. 4 is a diagram illustrating the acquisition of the projection image Gi. As shown in FIG. 4, the radiation source 16 is moved to each radiation source position of S1, S2, . . . , Sn, the radiation source 16 is driven at each radiation source position to irradiate the breast M with radiation, and the radiation transmitted through the breast M are detected by the radiation detector 15. As a result, the projection images G1, G2, . . . , Gn are acquired corresponding to the radiation source positions S1 to Sn. At each of the radiation source positions S1 to Sn, radiation of the same dose are emitted to the breast M. The plurality of acquired projection images Gi are stored in the storage 23. The plurality of projection images Gi may be acquired by a program separate from the tomosynthesis imaging support program and stored in the storage 23 or the external storage device. In this case, the image acquisition unit 40 reads the plurality of projection images Gi stored in the storage 23 or the external storage device from the storage 23 or the external storage device for reconstruction processing and the like.

In FIG. 4, the radiation source position Sc is a radiation source position where an optical axis XO of the radiation emitted from the radiation source 16 is perpendicular to the detection surface 15A of the radiation detector 15. The radiation source position Sc is referred to as a reference radiation source position Sc, and the projection image Gc acquired by irradiating the breast M with radiation at the reference radiation source position Sc is referred to as a reference projection image Gc. Here, "the optical axis XO of the radiation is perpendicular to the detection surface 15A of the radiation detector 15" means that the optical axis XO of the radiation crosses the detection surface 15A of the radiation detector 15 at an angle of 90°. However, without being limited to this, a case where the optical axis XO of the radiation crosses the detection surface 15A of the radiation detector 15 with a certain degree of error with respect to 90° may be included. For example, a case where the optical axis XO of the radiation crosses the detection surface 15A of the radiation detector 15 with an error of about ±3° with respect to 90° is included in "the optical axis XO of the radiation is perpendicular to the detection surface 15A of the radiation detector 15" in the present embodiment.

Figure 5:
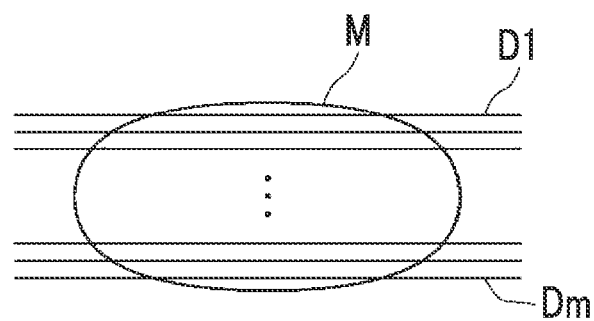
FIG. 5 is a diagram illustrating the generation of a tomographic image.

The reconstruction unit 41 reconstructs all or part of the plurality of projection images Gi to generate the tomographic image in which a desired tomographic plane of the breast M is emphasized. Specifically, the reconstruction unit 41 reconstruct all or part of the plurality of projection images Gi by a well-known back projection method such as a simple back projection method or a filtered back projection method to generate a plurality of tomographic images Dj (j=1 to m, m is the number of tomographic images) on each of a plurality of tomographic planes of the breast M, as shown in FIG. 5. In this case, a three-dimensional coordinate position in a three-dimensional space including the breast M is set, pixel values of corresponding pixel positions of the plurality of projection images Gi are reconstructed for the set three-dimensional coordinate position, and the pixel value of the coordinate position is calculated. In a case where the positional shift amount based on body movement of the breast M in the tomosynthesis imaging is derived as described later, the reconstruction unit 41 corrects the positional shift amount and reconstructs the plurality of projection images Gi to generate a corrected tomographic image in which body movement is corrected.

The information acquisition unit 31 acquires at least one information item of the subject information indicating the feature of the breast M which is a subject, the imaging condition information indicating the imaging condition at the time of the tomosynthesis imaging, or the positioning information indicating the positioning of the breast M. In the present embodiment, all the subject information, the imaging condition information, and the positioning information are acquired. These information items are acquired by an operator's input using the input unit 4. The information items are also acquired by receiving information output by the imaging unit 10. These information items may be acquired from the external storage device in which the information items are stored.

The subject information includes at least one of a size of the breast M included in the projection image Gi, a thickness of the breast M, a type of the breast M, or information specifying a patient. The size of the breast M is a size of a region of the breast M included in the projection image Gi, and can be calculated by the number of pixels of the region of the breast M×an area of one pixel. The size of the breast M may be the size of the breast M in one projection image Gi, or may be a representative value such as an average value or a maximum value of the sizes of the breasts M included in the plurality of projection images Gi. The thickness of the breast M is the compression thickness of the breast M by the compression plate 17. The compression thickness is acquired by the imaging unit 10. The information specifying a patient includes a patient ID, a patient name, and the like.

On the other hand, the breast M is a mixture of a mammary gland tissue and an adipose tissue. According to a ratio of the mammary gland tissue and the adipose tissue, and a distribution status of the mammary gland tissue and the adipose tissue, the breast M can be classified into four types of breast which are a high concentration type, a fatty type, a mammary gland dispersion type, and a homogeneous high concentration type. The type of breast M is any of these four types. In order to determine the type of breast, amounts of the mammary gland tissue and the adipose tissue contained in the breast M is required. The amounts of the mammary gland tissue and the adipose tissue contained in the breast M can be calculated by the method described in JP2010-253245A, for example. The method described in JP2010-253245A is the method in which a mammary gland content rate is calculated based on the relationship between a radiation amount reaching the radiation detector 15 directly without penetrating the breast M at the time of the imaging, a radiation amount reaching the radiation detector 15 by penetrating the breast M, an attenuation coefficient of the radiation by the fat, an attenuation coefficient of the radiation by the mammary gland, and the thickness of the breast M, and the amounts of the mammary gland tissue and the adipose tissue contained in the breast M is obtained based on the mammary gland content rate.

The imaging condition information includes at least one of an imaging time from the start to the end of the tomosynthesis imaging, a compression force of the breast M, an imaging direction of the breast M, or the information specifying a technician who performs imaging. The compression force of the breast M is a force (unit is, for example, newton [N]) that compresses the breast M by the compression plate 17, and is input by the imaging unit 10. The imaging direction of the breast M is CC or MLO. The information specifying the technician is a technician ID, a technician name, and the like.

As the positioning information, for example, an evaluation result of the positioning described in JP2010-051456A can be used. In the method described in JP2010-051456A, the positioning is evaluated as follows. First, the projection image is analyzed, and a breast, a mammary gland, a pectoralis major muscle, and a nipple are extracted from the projection image as an anatomical structure. Then, based on the extraction result of the structures, a plurality of evaluation items relating to positioning at the time of the imaging of the projection image are evaluated, and each evaluation item is scored. The positioning is comprehensively evaluated based on the scores of the plurality of evaluation items. As the evaluation items, the symmetry of the right and left breasts, the laterality of the nipple (whether the nipple is imaged from the side), the degree of inclusion of the pectoralis major muscle, the posterior mammary gland space, the lower breast, and the like are used. In the present embodiment, the score of each evaluation item is acquired as the positioning information.

The body movement feature acquisition unit 32 acquires the body movement feature information indicating the feature of body movement of the breast M which occurs at the time of the tomosynthesis imaging, according to the information acquired by the information acquisition unit 31. The body movement feature information includes at least one of the positional shift amount based on body movement between the plurality of projection images Gi, a representative value of the positional shift amount for each region in a case where the breast M is divided into a plurality of regions, or the classification of body movement according to the positional shift amount. In the present embodiment, the classification of body movement derived from the positional shift amount is acquired as the body movement feature information, but the present invention is not limited thereto. In addition, in the present embodiment, the body movement feature acquisition unit 32 acquires the body movement feature information with reference to a database generated as described later. Additionally, in the present embodiment, the body movement feature information is derived by the body movement feature derivation unit 42 and registered in the database. Furthermore, the database is stored in the storage 23 by body movement feature derivation unit 42.

Hereinafter, processing for deriving the body movement feature information will be described. In order to derive the body movement feature information, the projection image Gi and the positional shift amount between the projection images Gi based on body movement of the breast M are required. For this reason, firstly, the image acquisition unit 40 causes the imaging unit 10 to perform the tomosynthesis imaging to acquire a plurality of the projection images Gi. The reconstruction unit 41 generates the plurality of tomographic images Dj by reconstructing the projection images Gi. Then, the body movement feature derivation unit 42 detects the feature points from the plurality of tomographic images Dj. Hereinafter, the processing performed by the body movement feature derivation unit 42 will be described.

Figure 6:
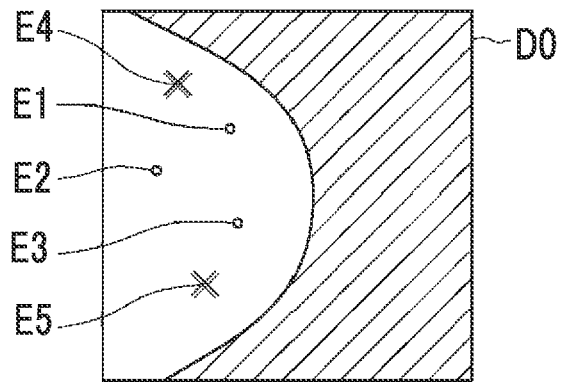
FIG. 6 is a diagram illustrating the detection of feature points from the tomographic image.

FIG. 6 is a diagram illustrating the detection of the feature points from the tomographic image. Here, the detection of the feature points from one tomographic image D0 will be described. As shown in FIG. 6, the tomographic image D0 includes point-like structures E1 to E3 such as calcification, and intersections E4 and E5 of edges such as intersections of blood vessels. The body movement feature derivation unit 42 detects the point-like structure, such as calcification, as a feature point from the tomographic image D0 by using an algorithm of known computer aided diagnosis (hereinafter, referred to as CAD). In addition, edges, intersections of edges, corners of edges, and the like included in the tomographic image D0 are detected as feature points by using an algorithm such as a Harris's corner detection method, a scale-invariant feature transform (SIFT), a features from accelerated segment test (FAST), or speeded up robust features (SURF). Then, the body movement feature derivation unit 42 calculates the projection position of the feature point in the projection image Gi. The feature point may be only one pixel in the tomographic image DO, or may be a plurality of pixels indicating the positions of feature structures.

Figure 7:
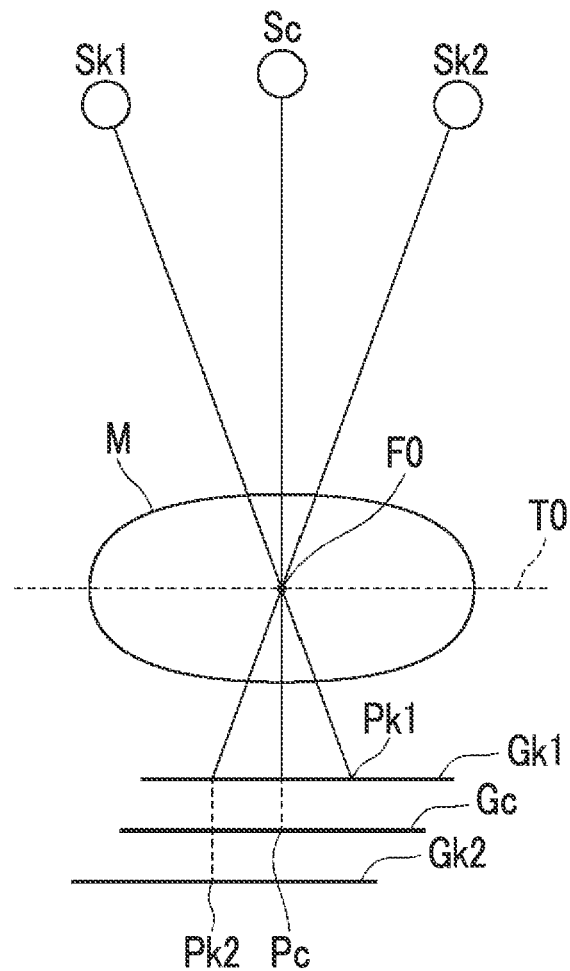
FIG. 7 is a diagram illustrating the calculation of a projection position of the feature points on the projection image.

FIG. 7 is a diagram illustrating the calculation of the projection position of the feature point on the projection image. In FIG. 7, in order to simplify the description, the calculation of the projection positions of a radiation source position Sk1, the reference radiation source position Sc, and a radiation source position Sk2 on corresponding three projection image Gk1, reference projection image Gc, and projection image Gk2 will be described. In FIG. 7, for the sake of description, the three projection images are shown so as to be present on different planes. In practice, however, the three projection images are present on the same plane. In FIG. 7, it is assumed that one feature point F0 is detected in the tomographic image D0 on a tomographic plane T0. Therefore, the feature point F0 is included in the tomographic plane T0. Here, for the sake of description, it is assumed that only one feature point F0 is projected. In practice, however, a plurality of different feature points are projected onto the projection image.

As shown in FIG. 7, at the time of the imaging, the feature point F0 included in the tomographic plane T0 of the breast M is projected to positions Pk1, Pc, and Pk2 in the projection image Gk1, the reference projection image Gc, and the projection image Gk2. The radiation source position Sk1, the reference radiation source position Sc, the radiation source position Sk2, and the position of the feature point F0 in the breast M in the three-dimensional space are known. In addition, the position of the detection surface 15A of the radiation detector 15, on which the projection image Gk1, the reference projection image Gc, and the projection image Gk2 are generated, in the three-dimensional space is also known. Therefore, the body movement feature derivation unit 42 calculates projection positions Pk1, Pc, and Pk2 of the feature point F0 at the radiation source position Sk1, the reference radiation source position Sc, and the radiation source position Sk2 based on the radiation source position Sk1, the reference radiation source position Sc, the radiation source position Sk2, and the position of the feature point F0 in the breast M in the three-dimensional space and the position of the detection surface of the radiation detector 15 where the projection image Gk1, the reference projection image Gc, and the projection image Gk2 are generated.

Figure 8:
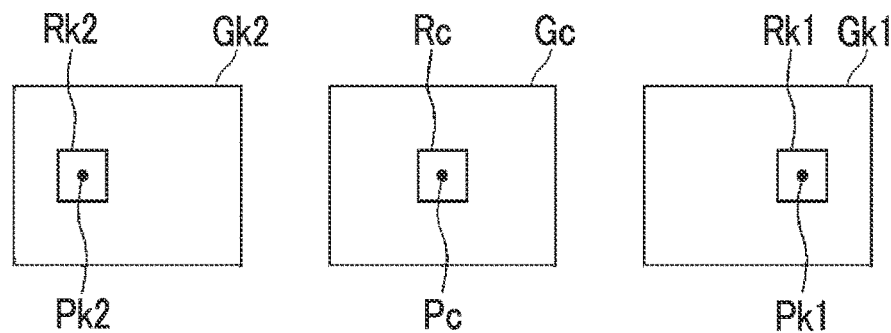
FIG. 8 is a diagram illustrating the setting of a region of interest.

Then, as shown in FIG. 8, the body movement feature derivation unit 42 sets regions of interest Rk1, Rc, and Rk2, which have predetermined sizes centering on the projection positions Pk1, Pc, and Pk2, in the projection image Gk1, the reference projection image Gc, and the projection image Gk2. Further, the body movement feature derivation unit 42 derives a shift vector between projection images acquired by successive imaging (hereinafter, referred to as between successive projection images) as the positional shift amount. First, using the reference projection image Gc as a reference, the registration of the region of interest Rk1 with respect to a region of interest Rc is performed in a predetermined search range including the region of interest Rc, and a shift vector representing the movement direction and the movement amount of the region of interest Rk1 with respect to the region of interest Rc is derived as the positional shift amount. In addition, using the projection image Gk2 as a reference, the registration of the region of interest Rc with respect to a region of interest Rk2 is performed in a predetermined search range including the region of interest Rk2, and a shift vector representing the movement direction and the movement amount of the region of interest Rc with respect to the region of interest Rk2 is derived as the positional shift amount. The registration means calculation of the movement direction and the movement amount of the region of interest Rk1 with respect to the region of interest Rc, and the movement direction and the movement amount of the region of interest Rc with respect to the region of interest Rk2 so that the correlation among the regions of interest Rc, Rk1, and Rk2 is maximized. Here, the normalized cross correlation may be used as the correlation. Additionally, the shift vector derived between successive projection images is one less than the number of projection images. For example, in a case where the number of projection images is 15, the number of shift vectors is 14. In a case where the number of projection images is 3, the number of shift vectors is 2.

Figure 9:
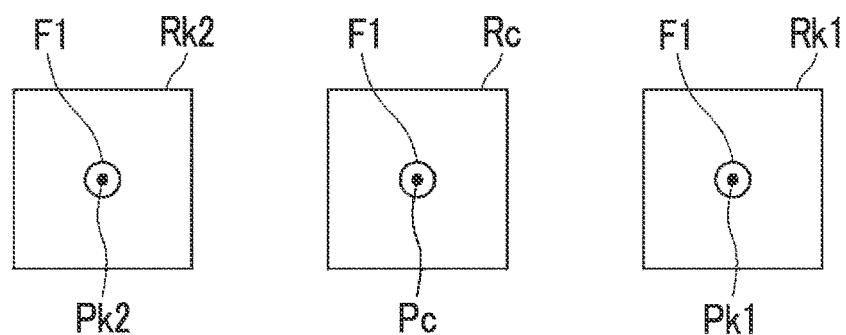
FIG. 9 is a diagram showing images in three regions of interest in a case where no body movement occurs.

FIG. 9 is a diagram showing images in the three regions of interest Rk1, Rc, and Rk2 in a case where no body movement occurs while acquiring the projection image Gk1, the reference projection image Gc, and the projection image Gk2. In FIG. 9, an image F1 of the feature point F0 included in the regions of interest Rk1, Rc, and Rk2 is shown by a circle larger than the projection positions Pk1, Pc, and Pk2. As shown in FIG. 9, in a case where no body movement occurs while acquiring the projection image Gk1, the reference projection image Gc, and the projection image Gk2, the projection positions Pk1, Pc, and Pk2 and the position of the image F1 of the feature point included in the regions of interest Rk1, Rc, and Rk2 match each other in all the three regions of interest Rk1, Rc, and Rk2. For this reason, the shift vector of the region of interest Rk1 with respect to the region of interest Rc, and the shift vector of the region of interest Rc with respect to the region of interest Rk2, that is, the positional shift amounts are all 0.

Figure 10:
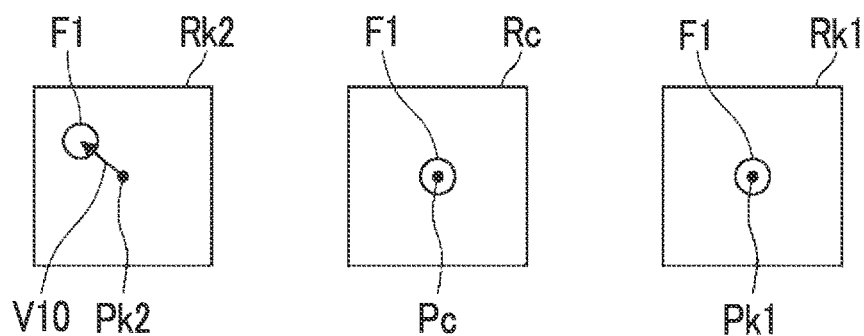
FIG. 10 is a diagram showing images in three regions of interest in a case where body movement occurs.

FIG. 10 is a diagram showing images in the three regions of interest Rk1, Rc, and Rk2 in a case where body movement occurs while acquiring the reference projection image Gc and the projection image Gk2 of the projection image Gk1, the reference projection image Gc, and the projection image Gk2. In FIG. 10, since no body movement occurs while acquiring the projection image Gk1 and the reference projection image Gc, the projection positions Pk1 and Pc in the regions of interest Rk1 and Rc and the position of the image F1 of the feature point included in the regions of interest Rk1 and Rc match each other. For this reason, the positional shift amount of the region of interest Rk1 with respect to the region of interest Rc is 0. On the other hand, since body movement occurs while acquiring the reference projection image Gc and the projection image Gk2, the projection position Pk2 in the region of interest Rk2 and the position of the image F1 of the feature point included in the region of interest Rk2 do not match each other. Therefore, due to the movement amount and the movement direction of the region of interest Rc with respect to the region of interest Rk2, a shift vector V10 having a size and a direction is derived. The derived shift vector V10 is the positional shift amount.

Figure 11:
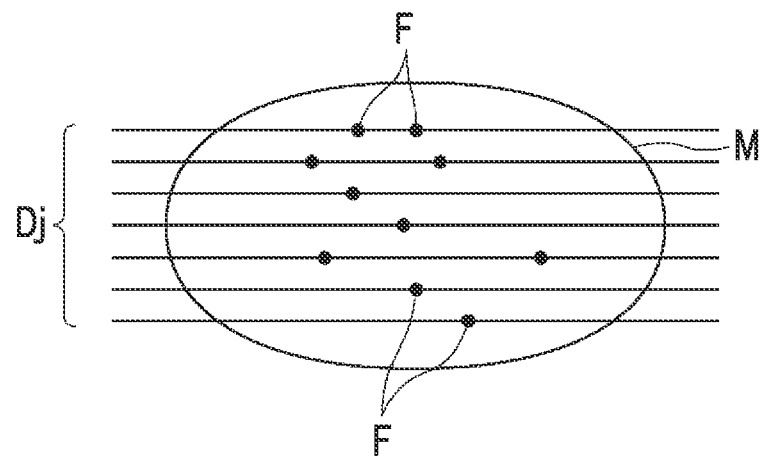
FIG. 11 is a diagram showing the feature points in a three-dimensional space.

In the above, one feature point F0 is detected in one tomographic image Dj, and the positional shift amount between the plurality of projection images is derived for only one feature point F0. In practice, however, as shown in FIG. 11, the body movement feature derivation unit 42 derives a positional shift amount for a plurality of different feature points F (here, ten feature points shown by black circles) in a three-dimensional space in the breast M expressed by the plurality of tomographic images Dj. As a result, for the projection image acquired in a state in which body movement occurs, positional shift amounts for a plurality of different feature points F are derived. The body movement feature derivation unit 42 interpolates the positional shift amounts for the plurality of different feature points F with respect to all the coordinate positions of the three-dimensional space for generating the tomographic image. As a result, for the projection image acquired in a state in which body movement occurs, the body movement feature derivation unit 42 derives the positional shift amounts for all the coordinate positions of the three-dimensional space for generating a tomographic image.

Figure 12:
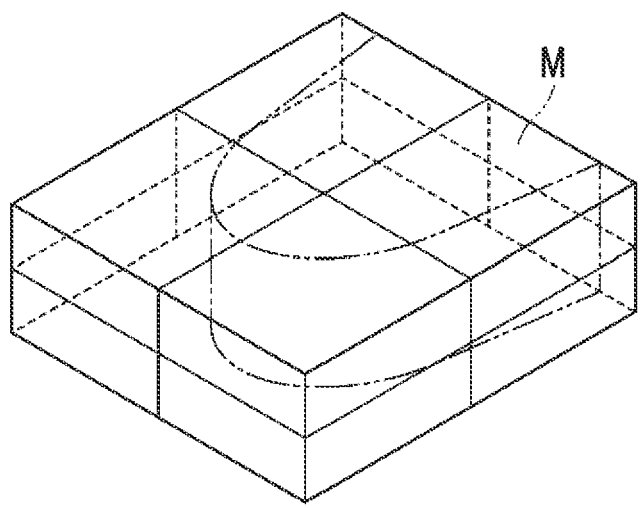
FIG. 12 is a diagram illustrating region division.

Further, the body movement feature derivation unit 42 equally divides the three-dimensional space for generating the tomographic image into eight regions. FIG. 12 is a diagram for illustrating a region division. As shown in FIG. 12, the body movement feature derivation unit 42 equally divides the three-dimensional space for generating the tomographic image into eight rectangular parallelepiped regions. Also, the number of region divisions is not limited to eight. Then, the body movement feature derivation unit 42 derives a representative value of the positional shift amount between the projection images as the region positional shift amount for each of the eight regions. As the representative value, an average value, a maximum value, a dispersion value, a median value, or the like of all the positional shift amounts derived in each region can be used. In the present embodiment, the maximum value and the dispersion value of the positional shift amount are used as the first and second region positional shift amounts respectively. Therefore, the first and second region positional shift amounts are derived in each of the eight regions.

In addition, the body movement feature derivation unit 42 derives a representative value of the first and second region positional shift amounts derived for each region, as the image positional shift amount for each projection image Gi. As the image positional shift amount, at least one of the average value or the dispersion value of the direction of the first and second region positional shift amounts in each of the eight regions, and at least one of the average value, the dispersion value, the maximum value, the median value, or the like of the magnitude (the scalar quantity) of the first and second region positional shift amounts can be used. In the present embodiment, the average value of the magnitude of the first and second region positional shift amounts in each of the eight regions is derived as the first and second image positional shift amounts respectively.

Additionally, the body movement feature derivation unit 42 derives the classification of body movement that has occurred at the time of the tomosynthesis imaging, based on the first and second image positional shift amounts. Specifically, in a case where the magnitude of the first image positional shift amount is equal to or greater than a predetermined first threshold Th1, the classification of body movement is set to the "rapid change".

In addition, in a case where the image positional shift amount is a dispersion value of the direction of the region positional shift amount, the classification of body movement is set to the "gradual movement in a certain direction" in a case where the image positional shift amount in any region is equal to or smaller than a predetermined second threshold Th2.

Additionally, in a case where the first image positional shift amount is equal to or smaller than a third threshold Th3 which is smaller than the threshold Th1, the classification of body movement is set to the "no body movement". Furthermore, the classification of body movement other than these three classifications of body movement is set to the "random".

Figure 13:
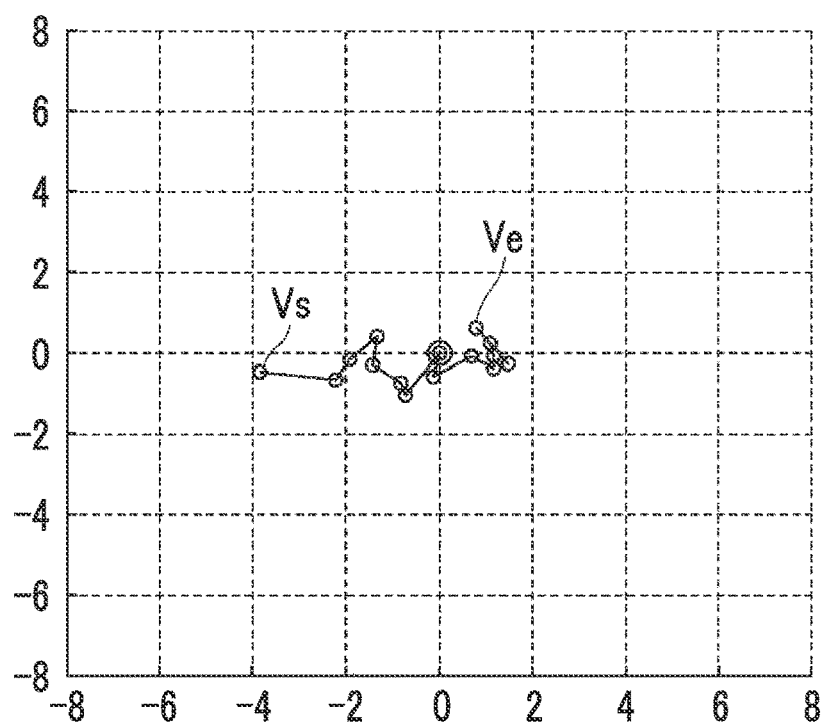
FIG. 13 is a diagram indicating a region positional shift amount for a certain region two-dimensionally.
Figure 14:
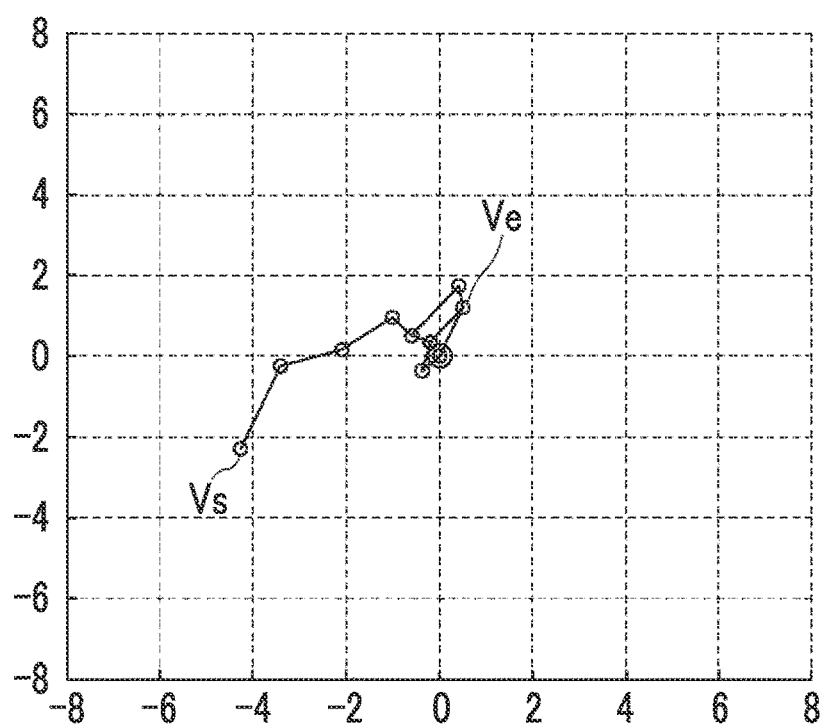
FIG. 14 is a diagram indicating a region positional shift amount for a certain region two-dimensionally.
Figure 15:
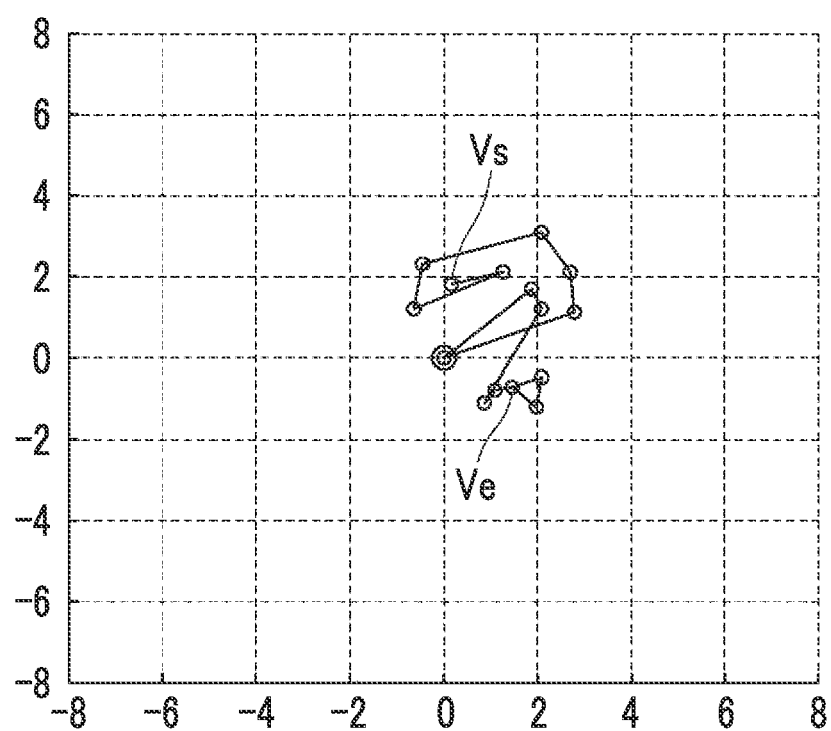
FIG. 15 is a diagram indicating a region positional shift amount for a certain region two-dimensionally.

FIGS. 13 to 15 are diagrams indicating a positional shift amount for a certain region among the eight regions two-dimensionally. In FIGS. 13 to 15, the lateral axis and the vertical axis represent an X direction and a Y direction of the projection image Gi, respectively. In addition, in FIGS. 13 to 15, fourteen positional shift amounts derived from fifteen projection images for a certain region are plotted with white circles. Additionally, an eighth projection image G8 is set as the reference projection image Gc, and the region positional shift amount thereof is plotted with a double circle at the origin (0, 0). Furthermore, reference symbols of Vs and Ve are respectively given to the region positional shift amount of the projection image to be first imaged and the positional shift amount of the projection image to be last imaged.

In FIG. 13, it can be considered that the dispersion value in the Y direction of the positional shift amount between the projection images is equal to or smaller than the second threshold Th2. This means that body movement occurs in the X direction. For this reason, the classification of body movement is to be the "gradual movement in a certain direction". Also, body movement that is gradually moved in a certain direction is likely to occur in a case where the imaging method is MLO imaging or the compression force is insufficient.

In FIG. 14, the positional shift amount between the projection image acquired by the first imaging and the projection image acquired by the fourth imaging is larger than the positional shift amount between the projection images acquired by the other imaging. In this case, the average value of the maximum value of the magnitude of the positional shift amount for each of the eight regions can be regarded as being equal to or greater than the first threshold Th1. For this reason, the classification of body movement is to be the "rapid change". The rapidly changing body movement is likely to occur, for example, in a case where a patient is surprised due to the start of movement of the radiation source 16 at the time of imaging.

In FIG. 15, since the relationship between the positional shift amounts in each of the projection images randomly appears, the classification of body movement is to be the "random".

Figure 16:
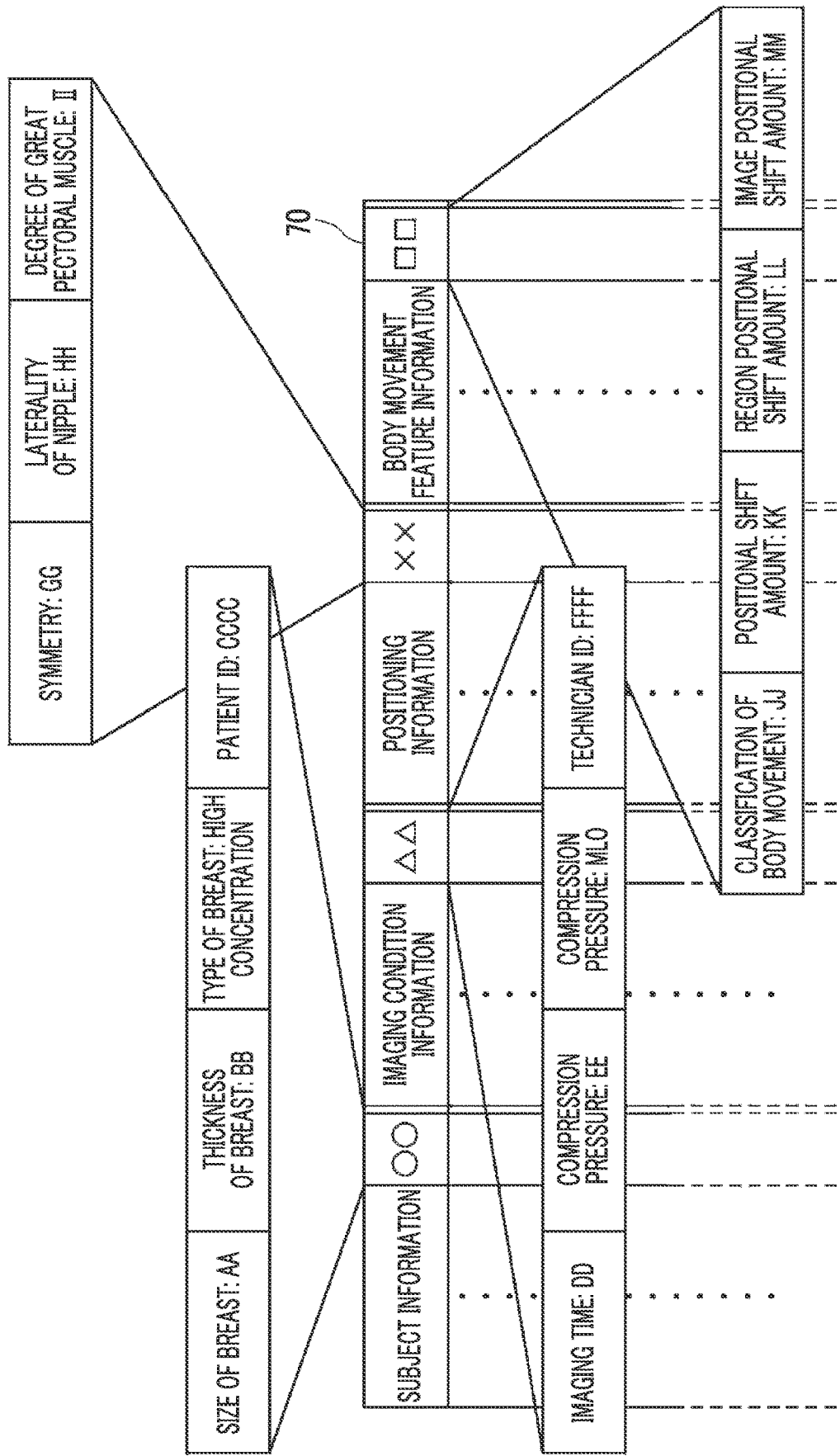
FIG. 16 is a diagram showing a database in which the body movement feature information corresponds to subject information, imaging condition information, and positioning information.

The body movement feature derivation unit 42 generates a database in which the classification of body movement derived as described above, the positional shift amount, the region positional shift amount, and the image positional shift amount, that is, the body movement feature information corresponds to the subject information, the imaging condition information, and the positioning information. FIG. 16 is a diagram showing the database in which the subject information, the imaging condition information, and the positioning information correspond to the body movement feature information. As shown in FIG. 16, in the database 70, a plurality of information items in which the subject information (a size and a thickness of the breast M, type of the breast, and a patient ID), the imaging condition information (an imaging time, a compression force, an imaging direction, and a technician ID), and the positioning information (an evaluation result of the positioning, here, symmetry, laterality of the nipple, and degree of the pectoralis major muscle) correspond to the body movement feature information (classification of body movement, positional shift amount, region positional shift amount, and image positional shift amount) are registered. Also, the database 70 corresponds to the correspondence information of the present disclosure. The database 70 generated in this way is stored in the storage 23. In a case where a new projection image is acquired, the subject information, the imaging condition information, the positioning information, and the body movement feature information for the tomosynthesis imaging in which a new projection image is acquired are newly registered in the database 70.

The body movement feature acquisition unit 32 acquires the body movement feature information with reference to the database 70 according to at least one of the subject information, the imaging condition information, or the positioning information which are acquired by the information acquisition unit 31.

Also, in the database 70 shown in FIG. 16, the body movement feature information corresponds to the subject information, the imaging condition information, and the positioning information. However, the database 70 may be generated such that the body movement feature information corresponds to any one or two information items of the subject information, the imaging condition information, or the positioning information. In this case, the information acquisition unit 31 acquires one or two information items according to the information registered in the database 70.

The advice derivation unit 33 derives an imaging advice at the time of the tomosynthesis imaging according to the body movement feature information acquired by the body movement feature acquisition unit 32. In addition, in the present embodiment, the advice derivation unit 33 derives the imaging advice further using at least one information item of the subject information, the imaging condition information, or the positioning information. Therefore, the advice derivation unit 33 includes a learned model in which learning is performed such that the imaging advice is output by inputting the body movement feature information, or inputting the body movement feature information and at least one information item of the subject information, the imaging condition information, or the positioning information.

The learned model is created by learning a deep neural network using the imaging advice corresponding to the body movement feature information, and the imaging advice in which the body movement feature information corresponds to at least one information item of the subject information, the imaging condition information, or the positioning information as teacher data.

FIG. 17 is a diagram showing an example of the teacher data. As shown in FIG. 17, in a case where the classification of body movement is the "gradual movement in a certain direction" and the compression force which is one of the imaging condition information items is equal to or smaller than the threshold value, teacher data 51 causes the imaging advice of "In the previous imaging, body movement being gradually moved in a certain direction occurs under the compression force X [N]. Please take an image with increased compression force." to be output. In a case where the classification of body movement is the "rapid change", teacher data 52 causes the imaging advice of "In the previous imaging, body movement rapidly changing occurs. Please ask a patient not to suddenly move during imaging and take an image." to be output. In a case where the classification of body movement is other than the "no body movement", the type of the breast which is one of the subject information items is the "fatty breast", or the thickness of the breast M which is one of the subject information items is equal to or greater than the threshold value, teacher data 53 causes the imaging advice of "it is a breast that body movement is likely to occur. Please take an image with attention to a compression force and positioning." to be output. In a case where the classification of body movement is the "gradual movement in a certain direction", the imaging direction which is one of the imaging condition information items is MLO, and the pectoralis major muscle area which is one of the positioning information items is equal to or greater than the threshold value, teacher data 54 causes the imaging advice of "In the previous imaging, body movement being gradually moved in a certain direction occurs at the positioning in which the pectoralis major muscle is greatly reflected. Please pay attention to the positioning." to be output.

Also, the teacher data is not limited to that shown in FIG. 17. Any teacher data can be used as long as it is the imaging advice corresponding to the body movement feature information, or the imaging advice corresponding to the body movement feature information and at least one information item of the subject information, the imaging condition information, or the positioning information, temporary teacher data can be used.

The learned model is not limited to the deep neural network, and a support vector machine, a convolutional neural network, a recurrent neural network, and the like can be used.

The display controller 34 displays the imaging advice derived by the advice derivation unit 33 on the display unit 3. FIG. 18 is a diagram showing a display screen of the imaging advice. As shown in FIG. 18, a display screen 60 displays the imaging advice of, for example, "In the previous imaging, body movement rapidly changing occurs. Please ask a patient not to suddenly move during imaging and take an image." in addition to a patient ID and a patient name.

Figure 19:
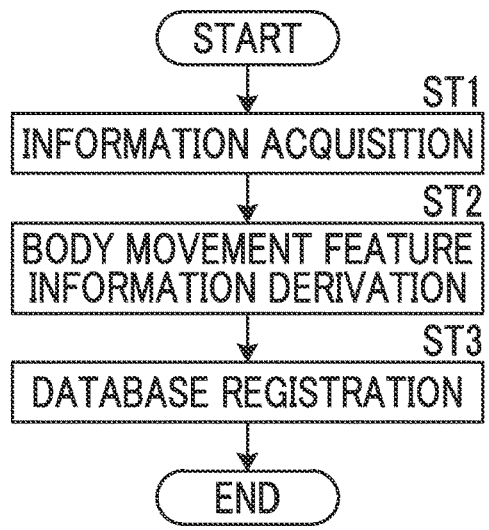
FIG. 19 is a flowchart showing processing for registering the body movement feature information in the database in the present embodiment.

Next, the processing performed in the present embodiment will be described. First, processing for registering the body movement feature information in the database 70 will be described. FIG. 19 is a flowchart showing the processing for registering the body movement feature information in the database in the present embodiment. The processing is started by the instruction of an operator to start the tomosynthesis imaging, and the information acquisition unit 31 acquires at least one information item of the subject information, the imaging condition information, or the positioning information (information acquisition; step ST1). Next, the body movement feature derivation unit 42 derives the body movement feature information (step ST2), and the subject information, the imaging condition information, and the positioning information correspond to the derived body movement feature information and are registered in the database 70 (step ST3). Then, the processing is terminated.

Figure 20:
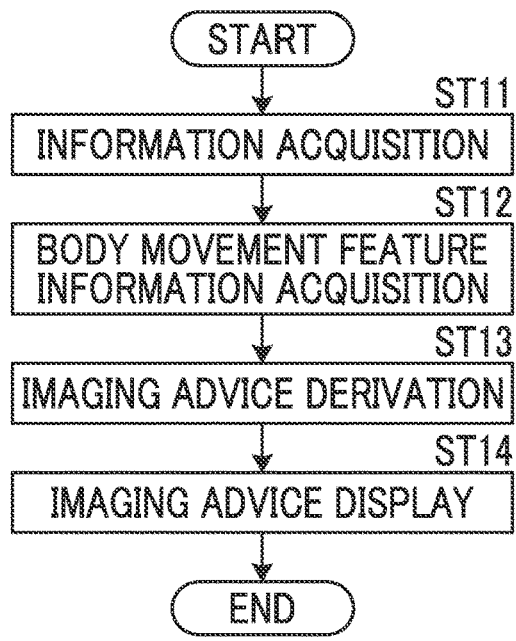
FIG. 20 is a flowchart showing processing for acquiring the body movement feature information and displaying the imaging advice in the present embodiment.

FIG. 20 is a flowchart showing processing for displaying the imaging advice by acquiring the body movement feature information in the present embodiment. The processing for acquiring the body movement feature information is performed before performing the tomosynthesis imaging. Also, It is assumed that the database 70 described above is already generated and stored in the storage 23. The processing is started by the instruction of an operator to start the tomosynthesis imaging, and the information acquisition unit 31 acquires at least one information item of the subject information, the imaging condition information, or the positioning information (information acquisition; step ST11). Next, the body movement feature acquisition unit 32 acquires the body movement feature information indicating the feature of body movement of the breast M which occurs at the time of the tomosynthesis imaging, according to information acquired by the information acquisition unit 31 (step ST12). Further, the advice derivation unit 33 derives the imaging advice at the time of the tomosynthesis imaging according to the body movement feature information acquired by the body movement feature acquisition unit 32 (step ST13). Then, the display controller 34 displays the imaging advice on the display unit 3 (step ST14), and the processing is terminated. The operator performs the tomosynthesis imaging based on the displayed imaging advice.

As described above, in the present embodiment, the body movement feature information indicating a feature of body movement of the subject that occurs at the time of tomosynthesis imaging is derived and registered in the database 70, according to at least one information item of the subject information, the imaging condition information, or the positioning information. In addition, in the present embodiment, in a case where new tomosynthesis imaging is performed, the body movement feature information is acquired with reference to the database 70. Therefore, by referring to the acquired body movement feature information, it is possible to appropriately estimate what kind of body movement occurs at the time of the tomosynthesis imaging.

In particular, since the imaging advice is derived according to the body movement feature information, the operator can properly recognize what should be taken care in order to prevent body movement at the time of the imaging by referring to the imaging advice. Further, by performing the tomosynthesis imaging according to the imaging advice, body movement can be reduced. As a result, a high-quality tomographic image in which blur caused by body movement is reduced can be generated.

Figure 21:
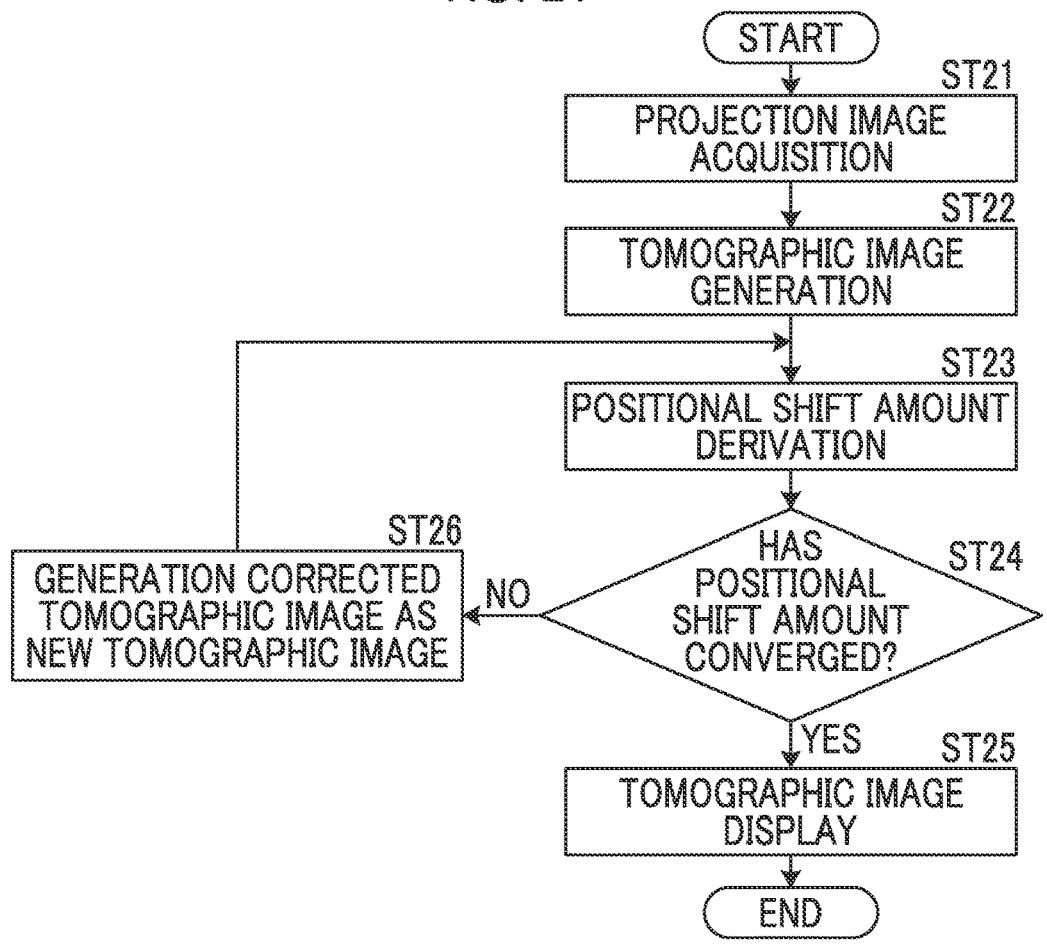
FIG. 21 is a flowchart showing processing of body movement correction in a case where the tomographic image is generated.

Even though the tomosynthesis imaging is performed according to the imaging advice, there is still a possibility that body movement occurs. Hereinafter, body movement correction in a case where the tomographic image is generated by reconstructing the projection image acquired by performing the tomosynthesis imaging will be described. FIG. 21 is a flowchart showing processing of the body movement correction in a case where the tomographic image is generated. In a case where the instruction of an operator to start the processing is received through the input unit 4, the image acquisition unit 40 causes the imaging unit 10 to perform the tomosynthesis imaging to acquire a plurality of projection images Gi (step ST21). Then, the reconstruction unit 41 reconstructs all or part of the plurality of projection images Gi to generate a plurality of tomographic images Dj (step ST22). Next, the body movement feature derivation unit 42 derives the positional shift amount between the plurality of projection images Gi (step ST23). The derivation of the positional shift amount is performed in the same manner as described above.

Further, the body movement feature derivation unit 42 determines whether or not the positional shift amount has converged (step ST24). The determination of whether or not the positional shift amount has converged may be performed by determining whether or not the positional shift amount derived for each projection image Gi has become equal to or smaller than a predetermined threshold Th10. The threshold Th10 may be set to a value at which it can be said that there is no influence of body movement on the tomographic image without correcting the positional shift amount any more. In this case, the positional shift amount may be all the positional shift amounts derived at the coordinate positions in the three-dimensional space, may be the region positional shift amount, or may be the image positional shift amount. In a case of YES in step ST24, it is unnecessary to correct the positional shift amount. Therefore, the display controller 34 displays the tomographic image (step ST25), and the processing is terminated.

In a case of NO in step ST24, the reconstruction unit 41 reconstructs the plurality of projection images Gi while correcting the positional shift amount, and thereby generates a corrected tomographic image Dhj as a new tomographic image (step ST26). Returning to the processing of step ST23, the body movement feature derivation unit 42 derives a new positional shift amount using a new tomographic image, and in step ST24, it is determined whether or not the positional shift amount is equal to or smaller than a predetermined the threshold Th10. The processing of step ST26 and step ST23 is repeated until it is determined as YES in step ST24. Also, in a case where the corrected tomographic image Dhj is generated as a new tomographic image, the tomographic image to be displayed in step ST26 is a new tomographic image.

Figure 22:
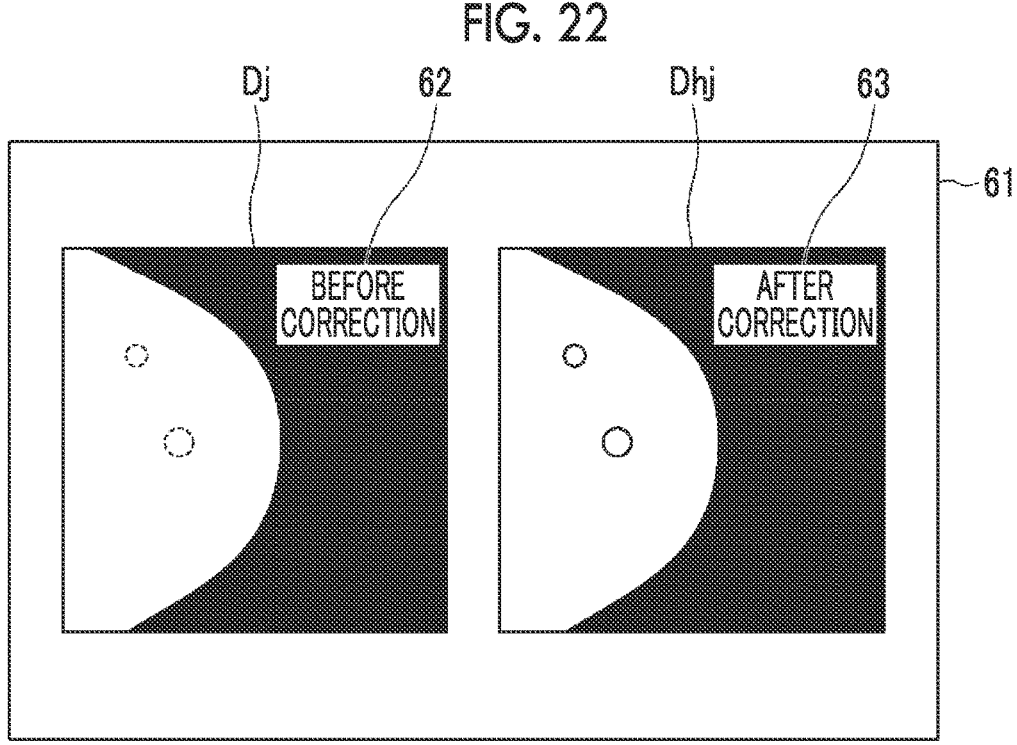
FIG. 22 is a diagram showing a display screen for a corrected tomographic image.

FIG. 22 is a diagram showing the display screen of the corrected tomographic image. As shown in FIG. 22, the tomographic image Dj before body movement correction and the corrected tomographic image Dhj subjected to body movement correction are displayed on a display screen 61. A label 62 of "before correction" is given to the tomographic image Dj so that it can be seen that the body movement is not corrected. A label 63 of "after correction" is given to the corrected tomographic image Dhj so that it can be seen that body movement has been corrected. The label 62 may be given only to the tomographic image Dj, or the label 63 may be given only to the corrected tomographic image Dhj. It is needless to say that only the corrected tomographic image Dhj may be displayed. In FIG. 22, a broken line indicates that the structure included in the tomographic image Dj before correction is blurred, and a solid line indicates that the structure included in the corrected tomographic image Dhj is not blurred.

Meanwhile, in the present embodiment, the positional shift amount, the region positional shift amount, or an image positional shift amount for each coordinate position in the three-dimensional space is registered in the database 70 as the body movement feature information. For this reason, the body movement feature acquisition unit 32 may acquire any positional shift amount registered in the database 70. Here, body movement often occurs in the same way for the same patient. For this reason, the positional shift amount acquired by the body movement feature acquisition unit 32 with reference to the database 70 based on the patient ID, or the like indicates body movement that is highly likely to occur in the patient. Therefore, in a case of performing the above-described body movement correction processing shown in FIG. 21, it is possible to use the positional shift amount acquired by the body movement feature acquisition unit 32 as an initial value of the positional shift amount. As a result, in a case where correction of the positional shift amount is repeated until the positional shift amount converges as in the body movement correction processing shown in FIG. 21, the calculation for deriving the positional shift amount in step ST23 can be omitted at the time of first processing.

Also, the body movement feature acquisition unit 32 acquires the body movement feature information with reference to the database 70, but the present invention is not limited thereto. The body movement feature acquisition unit 32 may acquire body movement feature information from the learned model in which learning is performed such that the body movement feature information is output by inputting at least one information item of the subject information, the imaging condition information, or the positioning information. The learned model corresponds to the correspondence information of the present disclosure. The learned model is created by learning the deep neural network or the like using the body movement feature information corresponding to at least one information item of the subject information, the imaging condition information, or the positioning information as teacher data, and is stored in the storage 23.

Figure 23:
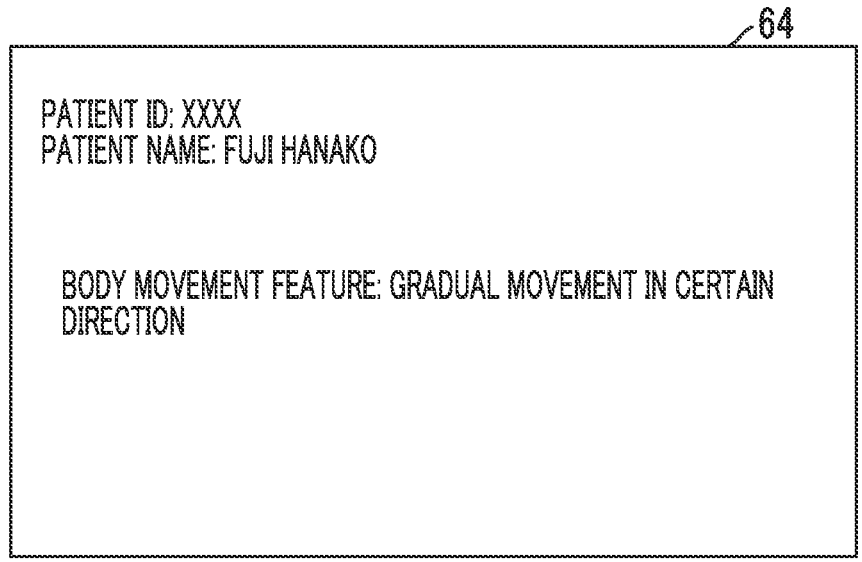
FIG. 23 is a diagram showing a display screen for the body movement feature information.

In the embodiments described above, the imaging advice is derived from the advice derivation unit 33 and is displayed on the display unit 3, but the present invention is not limited to thereto. In addition to the imaging advice or instead of the imaging advice, the body movement feature information acquired by the body movement feature acquisition unit 32 may be displayed on the display unit 3. In this case, for example, the body movement feature acquisition unit 32 may acquire only a patient ID as the subject information, and may acquire the body movement feature information with reference to the database 70 based on the patient ID. FIG. 23 is a diagram showing the display screen of the body movement feature information. As shown in FIG. 23, the "gradual movement in a certain direction" is displayed on the display screen 64 of the body movement feature information as a patient ID, a patient name, and a body movement feature.

In the embodiments described above, the positional shift amount is derived for all the coordinate positions of the three-dimensional space, but in a case where the three-dimensional space is equally divided into eight regions as shown in FIG. 12, one positional shift amount may be derived in each of the eight regions. In this case, by comparing with a case where the positional shift amount is derived for all the coordinate positions in the three-dimensional space, the amount of the calculation for deriving the positional shift amount can be reduced and the processing can be performed at high speed.

In the embodiments described above, the subject is the breast M, but the invention is not limited thereto. It is needless to say that any part such as the chest or the abdomen of the human body may be the subject.

In the embodiment described above, for example, various processors shown below can be used as the hardware structures of processing units that execute various kinds of processing, such as the information acquisition unit 31, the body movement feature acquisition unit 32, the advice derivation unit 33, the display controller 34, the image acquisition unit 40, the reconstruction unit 41, and the body movement feature derivation unit 42. The various processors include not only the above-described CPU, which is a general-purpose processor that executes software (program) and functions as various processing units, but also a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of the various processors, or may be a combination of two or more processors of the same type or different types (for example, a combination of a plurality of FPGAs or a combination of a CPU and an FPGA). Alternatively, a plurality of processing units may be configured by one processor.

As an example of configuring a plurality of processing units by one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by one or more of the above-described various processors as a hardware structure.

More specifically, as the hardware structure of these various processors, it is possible to use an electrical circuit (circuitry) in which circuit elements such as semiconductor elements are combined.

In addition to the program, the disclosure also extends to a non-transitory recording medium in which the program is recorded.

What is claimed is:

1. A tomosynthesis imaging support apparatus comprising at least one processor and a storage, wherein the processor is configured to:
   acquire at least one information item of subject information indicating a feature of a subject, imaging condition information indicating imaging conditions at a time of tomosynthesis imaging, or positioning information indicating positioning of the subject in a case where a plurality of projection images corresponding to each of a plurality of radiation source positions are acquired by performing the tomosynthesis imaging in which a radiation source is moved relative to a detection unit in order to emit radiation to the subject at the plurality of radiation source positions according to movement of the radiation source;
   derive body movement feature information indicating a feature of body movement of the subject that occurs at the time of the tomosynthesis imaging,
   wherein the storage stores correspondence information in which at least one information item of the subject information, the imaging condition information, or the positioning information corresponds to the body movement feature information;
   acquire at least one information item of new subject information, new imaging condition information, or new positioning information, and acquires the body movement feature information indicating the feature of body movement of the subject that occurs at the time of new tomosynthesis imaging according to the acquired information, with reference to the correspondence information before performing the tomosynthesis imaging;

derive an imaging advice at the time of the tomosynthesis imaging according to the acquired body movement feature information; and display, at the time of the tomosynthesis imaging, the acquired body movement feature information or the imaging advice, wherein the subject is a breast, and wherein the imaging advice includes advice regarding what kind of body movement occurs at least based on the type of the breast.

2. The tomosynthesis imaging support apparatus according to claim 1, wherein the correspondence information is a database in which at least one information item of the subject information, the imaging condition information, or the positioning information corresponds to the body movement feature information.

3. The tomosynthesis imaging support apparatus according to claim 1, wherein the correspondence information is a learned model in which learning is performed such that the body movement feature information is output by inputting at least one information item of the subject information, the imaging condition information, or the positioning information.

4. The tomosynthesis imaging support apparatus according to claim 1, wherein the body movement feature information includes at least one of a positional shift amount based on the body movement between the plurality of projection images, a representative value of the positional shift amount for each region in a case where the subject is divided into a plurality of the regions, or classification of the body movement according to the positional shift amount.

5. The tomosynthesis imaging support apparatus according to claim 1, wherein the subject information includes at least one of a size of the breast included in the projection image, a thickness of the breast, a type of the breast, or information specifying a patient.

6. The tomosynthesis imaging support apparatus according to claim 1, wherein the imaging condition information includes at least one of an imaging time at the time of the tomosynthesis imaging, a compression force of the breast, an imaging direction of the breast, or information specifying a technician who performs imaging.

7. The tomosynthesis imaging support apparatus according to claim 1, wherein the processor derives the imaging advice according to at least one information item of the subject information, the imaging condition information, or the positioning information.

8. The tomosynthesis imaging support apparatus according to claim 1, wherein the processor displays the acquired body movement feature information.

9. The tomosynthesis imaging support apparatus according to claim 1, wherein the processor acquires the subject information, the imaging condition information and the positioning information.

10. A tomosynthesis imaging support method comprising:

acquiring at least one information item of subject information indicating a feature of a subject, imaging condition information indicating imaging conditions at a time of tomosynthesis imaging, or positioning information indicating positioning of the subject in a case where a plurality of projection images corresponding to each of a plurality of radiation source positions are acquired by performing the tomosynthesis imaging in which a radiation source is moved relative to a detection unit in order to emit radiation to the subject at the plurality of radiation source positions according to movement of the radiation source;

deriving body movement feature information indicating a feature of body movement of the subject that occurs at the time of the tomosynthesis imaging;

storing correspondence information in which at least one information item of the subject information, the imaging condition information, or the positioning information corresponds to the body movement feature information;

acquiring at least one information item of new subject information, new imaging condition information, or new positioning information, and acquiring the body movement feature information indicating the feature of body movement of the subject that occurs at the time of new tomosynthesis imaging according to the acquired information, with reference to the correspondence information before performing the tomosynthesis imaging;

deriving an imaging advice at the time of the tomosynthesis imaging according to the acquired body movement feature information; and displaying, at the time of the tomosynthesis imaging, the acquired body movement feature information or the imaging advice, wherein the subject is a breast, and wherein the imaging advice includes advice regarding what kind of body movement occurs at least based on the type of the breast.

11. A non-transitory computer-readable storage medium that stores a tomosynthesis imaging support program that causes a computer to execute:

a step of acquiring at least one information item of subject information indicating a feature of a subject, imaging condition information indicating imaging conditions at a time of tomosynthesis imaging, or positioning information indicating positioning of the subject in a case where a plurality of projection images corresponding to each of a plurality of radiation source positions are acquired by performing the tomosynthesis imaging in which a radiation source is moved relative to a detection unit in order to emit radiation to the subject at the plurality of radiation source positions according to movement of the radiation source;

a step of deriving body movement feature information indicating a feature of body movement of the subject that occurs at the time of the tomosynthesis imaging;

a step of storing correspondence information in which at least one information item of the subject information, the imaging condition information, or the positioning information corresponds to the body movement feature information;

a step of acquiring at least one information item of new subject information, new imaging condition information, or new positioning information, and acquiring the body movement feature information indicating the feature of body movement of the subject that occurs at the time of new tomosynthesis imaging according to the acquired information, with reference to the correspondence information before performing the tomosynthesis imaging;

a step of deriving an imaging advice at the time of the tomosynthesis imaging according to the acquired body movement feature information; and displaying, at the time of the tomosynthesis imaging, the acquired body movement feature information or the imaging advice, wherein the subject is a breast, and wherein the imaging advice includes advice regarding what kind of body movement occurs at least based on the type of the breast.

* * * * *